United States Patent
Hirotsu et al.

(10) Patent No.: US 8,247,583 B2
(45) Date of Patent: Aug. 21, 2012

(54) 3-ETHYLOXETHANE COMPOUND HAVING HYDROXYL GROUP AND METHOD FOR PRODUCING THE SAME

(75) Inventors: Kenji Hirotsu, Yamaguchi (JP); Tadashi Murakami, Yamaguchi (JP)

(73) Assignee: UBE Industries, Ltd., Yamaguchi (JP)

( * ) Notice: Subject to any disclaimer, the term of this patent is extended or adjusted under 35 U.S.C. 154(b) by 673 days.

(21) Appl. No.: 12/303,603

(22) PCT Filed: Jun. 5, 2007

(86) PCT No.: PCT/JP2007/061374
§ 371 (c)(1),
(2), (4) Date: Dec. 5, 2008

(87) PCT Pub. No.: WO2007/142236
PCT Pub. Date: Dec. 13, 2007

(65) Prior Publication Data
US 2010/0174098 A1    Jul. 8, 2010

(30) Foreign Application Priority Data

Jun. 6, 2006 (JP) ................ P2006-157742
Jun. 6, 2006 (JP) ................ P2006-157743
Apr. 5, 2007 (JP) ................ P2007-099351

(51) Int. Cl.
*C07D 305/06* (2006.01)
(52) U.S. Cl. .................................................. 549/510
(58) Field of Classification Search .............. None
See application file for complete search history.

(56) References Cited

FOREIGN PATENT DOCUMENTS

| JP | 2000-302774 | 10/2000 |
|----|-------------|---------|
| JP | 2001-163961 | 6/2001 |
| JP | 2004-051556 | 2/2004 |
| JP | 2005-320491 | 11/2005 |
| JP | 2006-028116 | 2/2006 |

OTHER PUBLICATIONS

Watanabe, caplus and 2007:225268.*
Bacher, E. et al., Synthesis and Characterization of Photo-Cross-Linkable Hole-Conducting Polymers, Macromolecules, 2005, vol. 38, No. 5, p. 1640-1647.
El-Ghayoury, A. et al., Ultraviolet-ultraviolet dual-cure process based on acrylate oxetane monomers, Journal of Polymer Science, Part A: Polymer Chemistry, 2003, vol. 41, No. 4, p. 469-475.

* cited by examiner

*Primary Examiner* — Sun Jae Loewe
(74) *Attorney, Agent, or Firm* — Fildes & Outland, P.C.

(57) ABSTRACT

Disclosed is a 3-ethyloxethane compound having a hydroxyl group which is represented by the following general formula (1). (1) (In the formula, A represents an alkylene group having 3-5 carbon atoms which may have an ether bond or an alkylene group having 3-5 carbon atoms which may be substituted by a hydroxyl group.) The 3-ethyloxethane compound having a hydroxyl group can be produced by reacting a 3-ethyloxethane compound represented by the general formula (2) below, a diol compound represented by the general formula (3) below and a base. (2) (In the formula, X represents a leaving group.) (3) (In the formula, A is as defined above.)

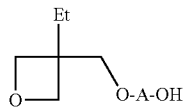

(1)

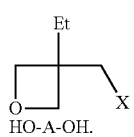

(2)

HO-A-OH.
(3)

4 Claims, No Drawings

3-ETHYLOXETHANE COMPOUND HAVING HYDROXYL GROUP AND METHOD FOR PRODUCING THE SAME

TECHNICAL FIELD

The present invention relates to a hydroxyl group-containing 3-ethyloxetane compound having low moisture absorption and high stability and a method of preparing the same. The hydroxyl group-containing 3-ethyloxetane compound is, for example, a compound which is useful as raw materials for preparing an active energy ray curing composition and an adhesive composition (cf., for example, Patent Document 1 and 2).

Patent Document 1: JP-A-2001-163961
Patent Document 2: JP-A-2005-320491

BACKGROUND ART

As a process of producing the hydroxyl group-containing 3-ethyloxetane compound, for example, a method of reacting 3-ethyl-3-chloromethyloxetane and 1,6-hexanediol in N,N-dimethylformamide in the presence of sodium hydride to produce 3-ethyl-3-(6-hydroxyhexyl)oxymethyloxetane at yield 61% is disclosed conventionally (cf., for example, Non-patent Document 1). However, this method had the problem that sodium hydride associated with the complicated handling must be used. Said document does not mention any of oxetane compounds other than 3-ethyl-3-(6-hydroxyhexyl) oxymethyloxetane.

Also, as a reaction between a 3-ethyloxetane compound and a diol compound, known is, for example, a method of reacting a sulfonate ester of 3-alkyl-3-hydroxymethyloxetane and a diol in the presence of the base. But a material produced from any of substrates by this method is a bisoxetane ether compound (cf., for example, Patent Document 3). It was not possibly conceivable that the 3-ethyloxetane compound containing a hydroxyl group of the present invention can be provided by a reaction between the 3-ethyloxetane compound and the diol.

Non-patent Document 1: Macromolecules, 38, 1640 (2005)
Patent Document 3: JP-A-2000-302774

DISCLOSURE OF THE INVENTION

Problems to be Solved by the Invention

An object of the present invention is, that is, to solves said problems, and
(i) to provide a hydroxyl group-containing 3-ethyloxetane compound having low moisture absorption and high stability, and
(ii) to provide a method of producing a hydroxyl group-containing 3-ethyloxetane compound in high yield without the generation of a bisoxetane ether compound by a simple and easy method.

Means for Solving the Problems

The problem of the present invention is solved by a hydroxyl group-containing 3-ethyloxetane compound represented by the general formula (1):

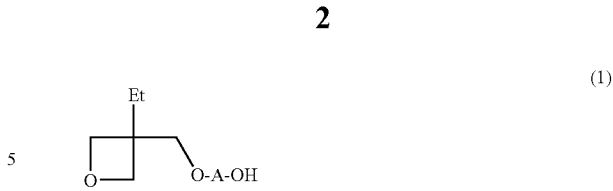

wherein A is an alkylene group having 3 to 5 carbon atoms which may have an ether bond, or an alkylene group having 3 to 5 carbon atoms which may be substituted with a hydroxyl group.

The problem of the present invention is solved also by a method of producing a hydroxyl group-containing 3-ethyloxetane compound, wherein said method comprises reacting a 3-ethyloxetane compound represented by the general formula (2):

wherein X is a leaving group,
a diol compound represented by the general formula (3):

wherein A is the same as defined above, and
a base.

Effects of the Invention

The hydroxyl group-containing 3-ethyloxetane compound of the present invention has low moisture absorption and high stability.

In addition, according to the production method of the present invention, the simple and easy procedure can produce the hydroxyl group-containing 3-ethyloxetane compound in high yield without generating a bisoxetane ether compound.

Modes for Carrying Out the Invention

In the hydroxyl group-containing 3-ethyloxetane compound represented by the general formula (1) of the present invention, A is the alkylene group having 3 to 5 carbon atoms which may have an ether bond, or an alkylene group having 3 to 5 carbon atoms which may be substituted with a hydroxyl group. The alkylene groups may be linear or branched. Preferably, a main chain (a linear chain) of A has 3 to 5 carbon atoms.

Specific examples of A include an alkylene group having 3 to 5 carbon atoms such as a trimethylene group, a tetramethylene group, a pentamethylene group, a —(CH(CH$_3$))—(CH$_2$)— group, a —(CH$_2$)—(CH(CH$_3$))—(CH$_2$)— group and a —(CH$_2$)—(CH(CH$_3$))—(CH$_2$)$_2$— group; an alkylene group having 3 to 5 carbon atoms containing an ether bond such as a —(CH$_2$)—O—(CH$_2$)$_2$— group and a —(CH$_2$)$_2$—O—(CH$_2$)$_2$— group; and an alkylene group having 3 to 5 carbon atoms containing a hydroxy group, such as a 2-hydroxypropylene group.

In the general formula (1), Et is an ethyl group.

The 3-ethyloxetane compound to be used in reaction of the present invention is represented by the general formula (2). In the general formula (2), X is the leaving group, and specific examples thereof include, for example, halogen atoms such as a chlorine atom, a bromine atom and a iodine atom; alkylsulfonyloxy groups (preferably, having 1 to 5 carbon atoms) such as a methanesulfonyloxy group, an ethanesulfonyloxy group and a trifluoromethanesulfonyloxy group; arylsulfonyloxy groups (preferably, having 6 to 15 carbon atoms) such as a benzenesulfonyloxy group and a p-toluene sulfonyloxy group. X is preferably the halogen atom or the alkylsulfonyloxy group, more preferably the bromine atom or the methanesulfonyloxy group.

The diol compound to be used in the reaction of the present invention is represented by the general formula (3). In the general formula (3), A is same as defined above, and specific examples of the diol compound to be used include, for example, 1,3-propanediol, 1,2-propanediol, 2-methyl-1,3-propanediol, 1,4-butanediol, 1,3-butanediol, 2-methyl-1,4-butanediol, 1,5-pentanediol, diethylene glycol and glycerin.

Preferably, a use amount of the diol compound is from 1 mol to 10 mol, more preferably from 1.5 mol to 5 mol, based on 1 mol of the 3-ethyloxetane compound.

Examples of the base to use in reaction of the present invention include lithium amides such as lithium diisopropylamide and lithium hexamethyldisilazide; alkali metal hydroxides such as sodium hydroxide and potassium hydroxide; alkali metal carbonates such as sodium carbonate and potassium carbonate; and alkali metal hydrogen carbonate such as sodium hydrogencarbonate and potassium hydrogencarbonate. Preferably the alkali metal hydroxide, more preferably sodium hydroxide is used. These bases may be used alone or in combination of two or more in admixture.

A use amount of the base is preferably from 0.5 mol to 5 mol, more preferably from 0.9 mol to 2 mol, based on 1 mol of the 3-ethyloxetane compound.

In the reaction of the present invention, an additive may be added to control the reactivity (for example, to increase the reactivity or to control a consecutive reaction (for constraining the generation of the bisoxetane ether compound)) of reactivity. Examples of the additive to be used include, for example, water; quaternary ammonium salts such as tetrabutylammonium bromide and benzyltriethylammonium chloride; quaternary phosphonium salts such as tetramethylphosphonium bromide and tetraphenylphosphonium bromide; crown ethers such as 18-crown-6 and 15-crown-5; and halide salts such as potassium iodide, sodium iodide and sodium bromide. These additives may be used alone or in combination of two or more in admixture.

A use amount of the additive is preferably from 0 to 0.2 mol, more preferably from 0.001 mol to 0.1 mol, based on 1 mol of the 3-ethyloxetane compound.

The reaction of the present invention can be performed in the presence or the absence of a solvent. If the reaction is not obstructed, the solvent to be used is not limited. Examples of the solvent include water; nitriles such as acetonitrile, propionitrile and benzonitrile; amides such as N,N-dimethylformamide, N,N-dimethylacetamide and N-methylpyrrolidone; ureas such as N,N'-dimethylimidazolidinone; sulfoxides such as the dimethyl sulfoxide; sulfones such as sulfolane; ethers such as diethyl ether, diisopropyl ether, tetrahydrofuran and dioxane; and aromatic hydrocarbons such as benzene, toluene and xylene. Preferably the aromatic hydrocarbons, more preferably toluene and xylene are used. These solvents may be used alone or in combination of two or more in admixture.

A use amount of the solvent is suitably adjusted depending on uniformity and stirring characteristics of the reaction liquid. Said amount is preferably from 0 to 100 g, more preferably from 1 g to 50 g, based on 1 g of the 3-ethyloxetane compound.

The reaction of the present invention is performed, for example, by a method of reacting the 3-ethyloxetane compound, the diol compound and the base in the solvent (the additive is added, if necessary) with stirring. In general, the reaction is performed in a liquid phase. The reaction temperature in such case is preferably 0-200° C., more preferably 50-150° C., and the reaction pressure is not limited in particular. It is preferable to adopt a method of adding the 3-ethyloxetane compound after mixing the diol compound, the base and the solvent (the additive is added, if necessary).

The reaction of the present invention can provide the hydroxyl group-containing 3-ethyloxetane compound. After the completion of the reaction, the 3-ethyloxetane compound can be isolated and/or refined by general methods such as a filtration, a neutralization, an extraction, a concentration, a distillation and a column chromatography.

EXAMPLES

The present invention is explained specifically by illustrating Examples, but the scope of the present invention is not limited to these Examples. Hereinafter, "%" means "% by mass" in the followings, unless specifically specified.

Reference Example 1

Synthesis of 3-ethyl-3-methanesulfonyloxymethyloxetane

After adding 3-ethyl-3-hydroxymethyloxetane (465 g (4.0 mol)), triethylamine (486 g (4.8 mol)) and toluene (1,840 ml) to a glass flask having an inner volume of 5,000 ml equipped with a stirrer, a thermometer and a dropping funnel, while keeping the liquid temperature at 5-10° C., methanesulfonyl chloride (504 g (4.4 mol)) was gradually added to react at the same temperature for 3 hours and at room temperature for 3 hours with stirring. After the completion of the reaction, an aqueous saturated sodium bicarbonate solution (930 ml) was added to the reaction solution and a liquid separation was performed. Subsequently an aqueous layer was extracted with toluene (930 ml), an extract was combined with a previously extracted organic layer, and the combined liquid was washed with water (465 ml). A resultant organic layer was concentrated under reduced pressure to give, as a brown liquid, 3-ethyl-3-methanesulfonyloxymethyloxetane (777 g) having a purity of 95% (a value measured by $^1$H-NMR) (an isolated yield based on 3-ethyl-3-hydroxymethyloxetane: 95%).

The physical properties of 3-ethyl-3-methanesulfonylmethyloxetane were as follows.

CI-MS (m/e); 195 (M+1)

$^1$H-NMR (CDCl$_3$, δ (ppm)); 0.94 (3H, t), 1.81 (2H, q), 3.07 (3H, s), 4.38 (2H, s), 4.42-4.48 (4H, m)

Reference Example 2

Synthesis of 3-ethyl-3-chloromethyloxetane

After adding 3-ethyl-3-hydroxymethyloxetane (58.0 g (0.5 mol)), acetonitrile (300 ml) and triethylamine (61.0 g (0.60 mol)) to a glass flask having an inner volume of 1,000 ml equipped with a stirrer, a thermometer, a dropping funnel and a reflux condenser, while keeping liquid temperature at about 0° C., methanesulfonyl chloride (63 g (0.55 mol)) was gradually added to react at the same temperature for 3 hours with stirring. After the temperature was raised to room temperature, methanol (200 ml) was added and the reaction was further performed at 50° C. for 5 hours. After the completion of the reaction, a reaction solution was concentrated, ethyl acetate (200 ml) and water (100 ml) were added to a concentrate, and a liquid separation was performed. Subsequently after ethyl acetate (100 ml) was added an aqueous layer to perform the extraction, an extract was combined together with a previously extracted organic layer, and the mixture liquid was washed with water (100 ml). A resultant organic layer was concentrated under reduced pressure, and lithium chloride (23.2 g (0.55 mol)) and methanol (200 ml) were added to perform the reaction at room temperature for 5 hours and at 60° C. for 6 hours with stirring. After the completion of the reaction, the mixture was cooled to room temperature and a generated salt was filtered. A resultant filtrate was concentrated under reduced pressure, ethyl acetate (200 ml) and water (100 ml) were added to a concentrate, and a liquid separation was performed. Subsequently after ethyl acetate (100 ml) was added to an aqueous layer to perform an extraction, an extract was combined together with a previously extracted organic layer, and the mixture liquid was washed with water (100 ml). A resultant organic layer was distilled under reduced pressure (3.5 kPa, 79-80° C.) to give, as a colorless liquid, 3-ethyl-3-chloromethyloxetane having a purity of 99.6% (an analysis value by a gas chromatography) (44.2 g) (an isolated yield based on 3-ethyl-3-hydroxymethyloxetane: 65%).

The physical properties of 3-ethyl-3-chloromethyloxetane were as follows.

CI-MS (m/e); 135 (M+1)
$^1$H-NMR (CDCl$_3$, δ (ppm)); 0.90 (3H, t), 1.85 (2H, q), 3.79 (2H, s), 4.42 (4H, s)

Reference Example 3

Synthesis of 3-ethyl-3-p-toluenesulfonyloxymethyloxetane

After adding p-toluene sulfonyl chloride (229 g (1.2 mol)), benzyltriethylammonium chloride (17.1 g (75 mmol)) and toluene (450 ml) to a glass flask of an inner volume of 2,000 ml equipped with a stirrer, a thermometer, a dropping funnel and a reflux condenser, while keeping the liquid temperature below 5° C., a 35% aqueous sodium hydroxide solution (200 g (1.75 mol)) was gradually added. While keeping the liquid temperature below 10° C., 3-ethyl-3-hydroxymethyloxetane (116.2 g (1.0 mol)) was dropwise added to perform the reaction at the same temperature for 1 hour and at room temperature for 5 hours. After the completion of the reaction, toluene (150 ml) and water (250 ml) were added to a reaction solution and a liquid separation was performed. After washing a resultant organic layer with water (250 ml) twice, a magnesium sulphate was added so that the organic layer was dried. After the completion of drying, the organic layer was filtered and a resultant filtrate was concentrated under reduced pressure to give, as a colorless liquid, 3-ethyl-3-p-toluene sulfonyloxymethyloxetane having a purity of 90% (a value measured by $^1$H-NMR) (285 g) (an isolated yield based on 3-ethyl-3-hydroxymethyloxetane standard: 95%).

The physical properties of 3-ethyl-3-p-toluenesulfonyloxymethyloxetane were as follows.

CI-MS (m/e); 271 (M+1)
$^1$H-NMR (CDCl$_3$, δ (ppm)); 0.82 (3H, t), 1.74 (2H, q), 2.45 (3H, s), 4.17 (2H, s), 4.29-4.37 (4H, m), 7.35-7.39 (2H, m), 7.79-7.83 (2H, m)

Reference Example 4

Synthesis of 3-ethyl-3-bromomethyloxetane

3-Ethyl-3-methanesulfonyloxymethyloxetane (389 g (1.9 mol)) having a purity of 95% synthesized by the same method as in Reference Example 1, lithium bromide monohydrate (220 g (2.1 mol)) and toluene (500 ml) were added to a glass flask having an inner volume of 1,000 ml equipped with a stirrer, a thermometer and a dropping funnel. The mixture was reacted at 60-70° C. for 10 hours with stirring, lithium bromide monohydrate (21 g (0.2 mol)) was added, and the reaction was performed at the same temperature for 8 hours. After the completion of reaction, water (100 ml) was added to a reaction solution, and a liquid separation was performed. A resultant organic layer was distilled under reduced pressure (80-85° C., 2.7 kPa) to give, as a colorless liquid, 3-ethyl-3-bromomethyloxetane (291 g) having purity of 99% (an analysis value by a gas chromatography) (an isolated yield based on 3-ethyl-3-methanesulfonyloxymethyl-oxetane: 85%).

The physical properties of 3-ethyl-3-bromomethyloxetane were as follows.

CI-MS (m/e); 181 (M+3)
$^1$H-NMR (CDCl$_3$, δ (ppm)); 0.89 (3H, t), 1.87 (2H, q), 3.69 (2H, s), 4.37-4.43 (4H, m)

Example 1

Synthesis of 3-ethyl-3-(4-hydroxybutyl)oxymethyloxetane (hereinafter referred to as "HBOX")

1,4-Butanediol (721 g (8.0 mol)) and toluene (350 ml) were added to a glass flask having an inner volume of 2,000 ml equipped with a stirrer, a thermometer, a dropping funnel and an reflux condenser, and mixture was warmed to 60° C. with stirring. Tetrabutylammonium bromide (38.7 g (0.12 mol)) and 96% sodium hydroxide (184 g (4.4 mol)) were added, and the mixture warmed to 75° C. with stirring. Subsequently 3-ethyl-3-methanesulfonyloxymethyloxetane (777 g (3.8 mol)) having purity of 95% synthesized by the same method as in Reference Example 1 was dropwise added while keeping a liquid temperature at 75-85° C., and the mixture was reacted at the same temperature for 2 hours. After the completion of the reaction, water (800 ml) was added to the reaction liquid (a bisoxetane ether compound generated in the amount of only 7% (an analysis value by a gas chromatography)), and a liquid separation was performed to give an organic layer. Toluene (800 ml) and water (400 ml) were added to a resultant organic layer, and acetic acid was added with stirring so that pH was adjusted to 9.5. After a liquid separation, an aqueous layer was extracted with toluene (400 ml) twice. An extract (a toluene layer) and an organic layer were combined, and the resultant was concentrated under reduced pressure. A resultant concentrate was distilled under reduced pressure (157-159° C., 1.9 kPa) to give, as a colorless liquid, 3-ethyl-3-(4-hydroxybutyl)oxymethyloxetane having a purity of 96% (an analysis value by a gas chromatography) (497 g) (an isolated yield based on 3-ethyl-3-methane-sulfonyloxymethyloxetane: 67%).

3-Ethyl-3-(4-hydroxybutyl)oxymethyloxetane was a novel compound having the following physical properties.

CI-MS (m/e); 189 (M+1)
$^1$H-NMR (CDCl$_3$, δ (ppm)); 0.88 (3H, t, J=7.5), 1.58-1.68 (4H, m), 1.74 (2H, q, J=7.5), 3.47-3.60 (7H, m), 4.34 (2H, d, J=5.8), 4.44 (2H, d, J=5.8)

Example 2

Synthesis of 3-ethyl-3-(4-hydroxybutyl)oxymethyloxetane (HBOX)

1,4-Butanediol (721 g (8.0 mol)) and toluene (350 ml) were added to a glass flask having an inner volume of 2,000 ml equipped with a stirrer, a thermometer, a dropping funnel and a reflux condenser, and the mixture was warmed to 60° C. with stirring. 96% Sodium hydroxide (184 g (4.4 mol)) was added with stirring, the mixture was warmed to 75° C. Subsequently 3-ethyl-3-methanesulfonyloxymethyloxetane (777 g (3.8 mol)) having purity of 95% synthesized by the same method as in Reference Example 1 was dropwise added while keeping a liquid temperature at 75-85° C., the mixture was reacted at the same temperature for 2 hours. After the completion of the reaction, water (800 ml) was added to the reaction liquid (a bisoxetane ether compound generated in the amount of only 6% (an analysis value by a gas chromatography)), and a liquid separation was performed to give an organic layer. Toluene (800 ml) and water (400 ml) were added to a resultant organic layer, and acetic acid was added with stirring so that pH was adjusted to 9.5. After a liquid separation, an aqueous layer was extracted with toluene (400 ml) twice. An extract (a toluene layer) and an organic layer were combined, and the resultant was concentrated under reduced pressure. A resultant concentrate was distilled under reduced pressure (157-159° C., 1.9 kPa) to give, as a colorless liquid, 3-ethyl-3-(4-hydroxybutyl)oxymethyloxetane having a purity of 96% (an analysis value by a gas chromatography) (477 g) (an isolated yield based on 3-ethyl-3-methanesulfonyloxymethyloxetane: 64%).

Example 3

Synthesis of
3-ethyl-3-(4-hydroxybutyl)oxymethyloxetane
(HBOX)

1,4-Butanediol (270 g (3.0 mol)), 96% sodium hydroxide (36 g (0.86 mol)) and tetrabutylammonium bromide (3.6 g (11.2 mmol)) were added to a glass flask having an inner volume of 1,000 ml equipped with a stirrer, a thermometer, a dropping funnel and an reflux condenser, and the mixture was warmed to 50° C. Subsequently 3-ethyl-3-bromomethyloxetane (108 g (0.6 mol)) synthesized by the same method as in Reference Example 4 was dropwise added while keeping the liquid temperature at 50-60° C. After the completion of the reaction, heptane (100 ml) and water (100 ml) were added to the reaction liquid (a bisoxetane ether compound generated in the amount of only 3% (an analysis value by a gas chromatography)), and a liquid separation was performed. Subsequently, a resultant aqueous layer was extracted with toluene (200 ml) three times. An extract (a toluene layer) was washed with water (50 ml), and the resultant was concentrated under reduced pressure. After the completion of drying, it was filtered and a resultant filtrate was concentrated under reduced pressure to give, as a colorless liquid, 3-ethyl-3-(4-hydroxybutyl)oxymethyloxetane (75 g) having a purity of 95% (an analysis value by a gas chromatography) (an isolated yield based on 3-ethyl-3-bromomethyloxetane: 63%).

Example 4

Synthesis of
3-ethyl-3-(3-hydroxypropyl)oxymethyloxetane
(hereinafter, referred to as "HPROX")

1,3-Propanediol (285 g (3.7 mol)), tetrabutylammonium bromide (12.1 g (37.5 mmol)), 96% sodium hydroxide (72 g (1.7 mol)) and toluene (150 ml) were added to a glass flask having an inner volume of 1,000 ml equipped with a stirrer, a thermometer, a dropping funnel and a reflux condenser, and the mixture was warmed to 80° C. with stirring. Subsequently 3-ethyl-3-methanesulfonyloxymethyloxetane (324 g (1.5 mol)) having purity of 90% (a value measured by $^1$H-NMR) was dropwise added while keeping the liquid temperature at 80-90° C. After the completion of the reaction, water (300 ml) was added to the reaction liquid (a bisoxetane ether compound generated in the amount of only 7% (an analysis value by a gas chromatography)), and a liquid separation was performed to give an organic layer. Subsequently a resultant aqueous layer was extracted with toluene (200 ml), and an extract (a toluene layer) and an organic layer were mixed and concentrated under reduced pressure.

A resultant concentrate was distilled under reduced pressure (135-137° C., 1.1 kPa) to give, as a colorless liquid, 3-ethyl-3-(3-hydroxypropyl)oxymethyloxetane having a purity of 97% (an analysis value by a gas chromatography) (152 g) (an isolated yield based on 3-ethyl-3-methanesulfonyloxymethyloxetane: 56%).

3-Ethyl-3-(3-hydroxypropyl)oxymethyloxetane was a novel compound having the following physical properties.

CI-MS (m/e); 175 (M+1)
$^1$H-NMR (CDCl$_3$, δ (ppm)); 0.89 (3H, t, J=7.5), 1.73 (2H, q, J=7.5), 1.82-1.89 (2H, m), 2.37 (1H, t, J=5.5), 3.57 (2H, s), 3.66 (2H, t, J=5.6), 3.77 (2H, q, J=5.6), 4.39 (2H, d, J=5.9), 4.40 (2H, d, J=5.9)

Example 5

Synthesis of
3-ethyl-3-(5-hydroxypentyl)oxymethyloxetane
(hereinafter referred to as "HPENOX")

1,5-Pentanediol (1,171 g (11.2 mol)), tetrabutylammonium bromide (24.1 g (75 mmol)) and 96% sodium hydroxide (90 g (2.2 mol)) were added to a glass flask having an inner volume of 2,000 ml equipped with a stirrer, a thermometer, a dropping funnel and a reflux condenser, and the mixture was warmed to 70° C. with stirring. Subsequently 3-ethyl-3-methanesulfonyloxymethyloxetane (324 g (1.5 mol)) having a purity of 90% (a value measured by $^1$H-NMR) was dropwise added while keeping the liquid temperature at 75-85° C. to perform the reaction at the same temperature for 3 hours. After the completion of the reaction, the reaction solution was washed with heptane (200 ml), and then water (583 ml) was added and a liquid separation was performed. Water (1,166 ml) and toluene (500 ml) were added to a resultant organic layer, and a liquid separation was performed. Subsequently toluene (500 ml) was added to a resultant aqueous layer to perform the extraction, an extract (a toluene layer) and an organic layer were mixed, and a resultant mixture was washed at water (300 ml). Subsequently a resultant aqueous layer and an aqueous layer separated earlier were mixed, and a resultant mixture was extracted with toluene (500 ml). After washing an extract (a toluene layer) with water (300 ml), the extract was mixed with the previously obtained organic layer, and a resultant mixture was concentrated under reduced pressure. A resultant concentrate (a bisoxetane ether compound generated in the amount of only 14% (an analysis value by a gas chromatography)) was distilled under reduced pressure (136-140° C., 533 Pa) to give, as a colorless liquid, 3-ethyl-3-(5-hydroxypentyl)oxymethyloxetane having a purity of 93% (an analysis value by a gas chromatography) (109 g) (an isolated yield based on 3-ethyl-3-methanesulfonyloxymethyloxetane: 33%).

3-Ethyl-3-(5-hydroxypentyl)oxymethyloxetane was a novel compound having the following physical properties.

CI-MS (m/e); 203 (M+1)

$^1$H-NMR (CDCl$_3$, δ(ppm)); 0.88 (3H, t, J=7.5), 1.38-1.67 (6H, m), 1.74 (2H, q, J=7.5), 1.8 (1H, brs), 3.47 (2H, t, J=6.4), 3.52 (2H, s), 3.63 (2H, t, J=6.4), 4.34 (2H, d, J=5.8), 4.44 (2H, d, J=5.8)

Example 6

Synthesis of
3-ethyl-3-(2-hydroxyethyloxyethyl)oxymethyloxetane
(hereinafter, referred to as "HEOEOX")

Diethylene glycol (500 g (4.7 mol)), tetrabutylammonium bromide (5.0 g (15.5 mmol)) and 96% sodium hydroxide (50 g (1.2 mol)) were added to a glass flask having an inner volume of 1,000 ml equipped with a stirrer, a thermometer, a dropping funnel and a reflux condenser, and the mixture was warmed to 70° C. with stirring. Subsequently 3-ethyl-3-methanesulfonyloxymethyloxetane (216 g (1.0 mol)) having a purity of 90% (a value measured by $^1$H-NMR) was dropwise added and reacted for 2 hours while keeping the liquid temperature at 80-90° C. After the completion of the reaction, water (200 ml) was added to reaction liquid (a bisoxetane ether compound generated in the amount of only 9% (an analysis value by a gas chromatography)), and a liquid separation was performed to give an organic layer. Toluene (200 ml) and water (100 ml) were added to the resultant organic layer, and a liquid separation was performed. Subsequently a resultant aqueous layer was extracted with toluene (100 ml) twice. An extract (a toluene layer) and the previously obtained organic layer were mixed, and the mixture was concentrated under reduced pressure. A resultant concentrate was distilled under reduced pressure (142-145° C., 400 Pa) to give, as a colorless liquid, 3-ethyl-3-(2-hydroxyethyloxyethyl)oxymethyloxetane having a purity of 93% (an analysis value by a gas chromatography) (158 g) (an isolated yield based on 3-ethyl-3-methanesulfonyloxymethyloxetane: 72%).

3-Ethyl-3-(2-hydroxyethyloxyethyl)oxymethyloxetane was a novel compound having the following physical properties.

CI-MS (m/e); 205 (M+1)

$^1$H-NMR (CDCl$_3$, δ(ppm)); 0.89 (3H, t, J=7.5), 1.75 (2H, q, J=7.5), 2.5 (1H, brs), 3.57-3.85 (10H, m), 4.39 (2H, d, J=5.9), 4.46 (2H, d, J=5.9)

Example 7

Synthesis of
3-ethyl-3-(2,3-dihydroxypropyl)oxymethyloxetane
(hereinafter, referred to as "DHPOX")

Glycerin (138 g (1.5 mol)), benzyltriethylammonium chloride (2.4 g (11 mmol)) and 96% sodium hydroxide (24 g (0.58 mol)) were added to a glass flask of an inner volume of 300 ml equipped with a stirrer, a thermometer, a dropping funnel and a reflux condenser, and the mixture was warmed to 80° C. with stirring. Subsequently 3-ethyl-3-methanesulfonyloxymethyloxetane (102 g (0.5 mol)) having a purity of 95% prepared by the same method as in Reference Example 1 was gradually dropwise added while keeping the liquid temperature at 80-85° C. After the completion of the dropwise addition, 96% sodium hydroxide (6 g (0.14 mol)) was newly added, the mixture was further reacted at the same temperature for 2 hours. After the completion of the reaction, hydrochloric acid was added to a reaction solution so that pH was adjusted to 6.5. Ethyl acetate (150 ml) was added, and a liquid separation was performed. After the liquid separation, ethyl acetate (150 ml) was added to a resultant aqueous layer to perform an extraction, and an extract (an ethyl acetate layer) was combined with an organic layer and washed with an aqueous saturated sodium bicarbonate solution (20 ml), then concentrated under reduced pressure. A resultant concentrate was distilled under reduced pressure (147° C., 400-530 Pa) to give, as a colorless liquid, 3-ethyl-3-(2,3-dihydroxypropyl)oxymethyloxetane having a purity of 93% (an analysis value by a gas chromatography) (20 g) (an isolated yield based on 3-ethyl-3-methanesulfonyloxymethyloxetane: 20%).

3-Ethyl-3-(2,3-dihydroxypropyl)oxymethyloxetane was a novel compound having the following physical properties.

CI-MS (m/e); 191 (M+1)

$^1$H-NMR (CDCl$_3$, δ(ppm)); 0.89 (3H, t, J=7.5), 1.72 (2H, q, J=7.5), 2.59 (1H, brs), 3.11 (1H, brs), 3.55-3.79 (6H, m), 3.86-3.93 (1H, m), 4.41 (2H, d, J=5.8), 4.48-4.50 (2H, m)

Examples 8-10 and Comparative Example 1 (a Moisture Absorption Test of Oxetane)

10 g of each of 3-ethyl-3-(4-hydroxybutyl)oxymethyloxetane (HBOX) synthesized in Example 1, 3-ethyl-3-(3-hydroxypropyl)oxymethyloxetane (HPROX) synthesized in Example 4, 3-ethyl-3-(2,3-dihydroxypropyl)oxymethyloxetane (DHPOX) synthesized in Example 7 and 3-ethyl-3-hydroxymethyloxetane (hereinafter, referred to as EHO) which is a publicly known compound, was charged into a beaker of an inner volume of 50 ml and subjected to a moisture absorption test maintaining an environment at a humidity of 80% and at room temperature.

A change of water content (a change of mass %) of each oxetane at each elapsed time is shown in Table 1. The water content was measured by a titration-type water content measurement device (AQUACOUNTER AQ2100 manufactured by HIRANUMA SANGYO Co., Ltd.).

TABLE 1

| | | Elapsed time (hour) | | | | |
|---|---|---|---|---|---|---|
| | Oxetane | 0 | 12 | 24 | 41 | 101 |
| Example 8 | HBOX | 0.1 | 2.3 | 3.3 | 5.1 | 8.4 |
| Example 9 | HPROX | 0.1 | 2.2 | 3.4 | 5.4 | 8.9 |
| Example 10 | DHPOX | 0.05 | 2.5 | 4.3 | 6.3 | 11.3 |
| Com. Ex. 1 | EHO | 0.2 | 2.7 | 4.3 | 6.9 | 12.5 |

The above-mentioned results reveal that the oxetanes (HBOX and HPROX) of the present invention have lower moisture absorption than the well-known the oxetane (EHO).

Examples 11-18 and Comparative Examples 2-3

A Stability Test of Oxetane 10 g of each of 3-ethyl-3-(4-hydroxybutyl)oxymethyloxetane (HBOX) synthesized in Example 1, 3-ethyl-3-(3-hydroxypropyl)oxymethyloxetane (HPROX) synthesized in Example 4, 3-ethyl-3-(2-hydroxyethyloxyethyl)oxymethyloxetane (HEOEOX) synthesized in Example 6, 3-ethyl-3-(2,3-dihydroxypropyl)oxymethyloxetane (DHPOX) synthesized in Example 7 and 3-ethyl-3-hydroxymethyloxetane (hereinafter, referred to as EHO) which is a publicly known compound, was charged into a glass sample tube of an inner volume of 30 ml, and a cationic polymerization catalyst (SI-100L or SI-110L manufactured by SANSHIN CHEMICAL INDUSTRY CO., LTD.) (0.1 g) was added into the tube. The content of the tube was intimately mixed and left at room temperature. A state of each oxetane in each elapsed time was visually observed. The results are shown in Table 2.

TABLE 2

| | Oxetane | Cationic polymerization catalyst | Elapsed time (hour) | | | |
|---|---|---|---|---|---|---|
| | | | 24 | 48 | 72 | 96 |
| Example 11 | HBOX | SI-100L | Transparent | Transparent | Transparent | Transparent |
| Example 12 | | SI-110L | Transparent | Transparent | Transparent | Transparent |
| Example 13 | HPROX | SI-100L | Transparent | Transparent | Transparent | Transparent |
| Example 14 | | SI-110L | Transparent | Transparent | Transparent | Transparent |
| Example 15 | HEOEOX | SI-100L | Transparent | Transparent | Transparent | Transparent |
| Example 16 | | SI-110L | Transparent | Transparent | Transparent | Transparent |
| Example 17 | DHPOX | SI-100L | Transparent | Transparent | Transparent | Transparent |
| Example 18 | | SI-110L | Transparent | Transparent | Transparent | Transparent |
| Com. Ex. 2 | EHO | SI-100L | White opaque | White opaque | Gelled | Gelled |
| Com. Ex. 3 | | SI-110L | Transparent | White opaque | White opaque | Gelled |

The above-mentioned results reveal that the oxetanes (HBOX, HPROX, HEOEOX and DHPOX) of the present invention have excellent stability in comparison with the well-known the oxetane (EHO).

INDUSTRIAL APPLICABILITY

The present invention relates to hydroxyl group-containing 3-ethyloxetane compound having low moisture absorption and high stability and a method of preparing the same. The hydroxyl group-containing 3-ethyloxetane compound is, for example, a compound which is useful as production raw materials of an active energy ray curing composition and an adhesive composition.

The invention claimed is:

1. A hydroxyl group-containing 3-ethyloxetane compound represented by the general formula (1):

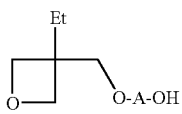
(1)

wherein A is an alkylene group having 3 to 5 carbon atoms which may have an ether bond, or an alkylene group having 3 to 5 carbon atoms which may be substituted with a hydroxyl group, provided that a main chain of A has 3 to 5 carbon atoms.

2. The hydroxyl group-containing 3-ethyloxetane compound according to claim 1, wherein A is a trimethylene group, a tetramethylene group, a pentamethylene group, a —(CH$_2$)—(CH(CH$_3$))—(CH$_2$)— group, a —(CH$_2$)—(CH(CH$_3$))—(CH$_2$)$_2$— group, a —(CH$_2$)—O—(CH$_2$)$_2$— group, a —(CH$_2$)$_2$—O—(CH$_2$)$_2$— group, or a 2-hydroxypropylene group.

3. A method of producing the hydroxyl group-containing 3-ethyloxetane compound according to claim 1, wherein said method comprises reacting a 3-ethyloxetane compound represented by the general formula (2):

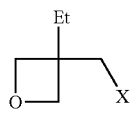
(2)

wherein X is a leaving group,
a diol compound represented by the general formula (3):

HO-A-OH  (3)

wherein A is an alkylene group having 3 to 5 carbon atoms which may have ether bond or an alkylene group having 3 to 5 carbon atoms which may be substituted with a hydroxyl group, provided that a main chain of A has 3 to 5 carbon atoms, and
a base.

4. The method according to claim 3, wherein A is a trimethylene group, a tetramethylene group, a pentamethylene group, a —(CH$_2$)—(CH(CH$_3$))—(CH$_2$)— group, a —(CH$_2$)—(CH(CH$_3$))—(CH$_2$)$_2$— group, a —(CH$_2$)—O—(CH$_2$)$_2$— group, a —(CH$_2$)$_2$—O—(CH$_2$)$_2$— group, or a 2-hydroxypropylene group.

* * * * *